United States Patent [19]

Hassall et al.

[11] 4,187,216

[45] Feb. 5, 1980

[54] DIPEPTIDE DERIVATIVES

[75] Inventors: Cedric H. Hassall, Welwyn; William H. Johnson, Hitchin; Noel A. Roberts, Welwyn Garden City, all of England

[73] Assignee: Hoffmann-La Roche Inc., Nutley, N.J.

[21] Appl. No.: 804,680

[22] Filed: Jun. 8, 1977

[30] Foreign Application Priority Data

Jun. 25, 1976 [GB] United Kingdom ............... 26662/76
Aug. 6, 1976 [GB] United Kingdom ............... 32847/76
Mar. 14, 1977 [GB] United Kingdom ............... 10657/77

[51] Int. Cl.$^2$ ..................... C07C 103/52; C07G 7/00
[52] U.S. Cl. ............................. 260/112.5 R; 424/177
[58] Field of Search ................ 260/112.5 R, 112.5 T, 260/561 A

[56] References Cited

FOREIGN PATENT DOCUMENTS 2649171 10/1976 Fed. Rep. of Germany .... 260/112.5 R

OTHER PUBLICATIONS

Thompson, R. C., (1974), Biochemistry, 13, 5495.
Chemical Abstracts, (1975), 106041p.
Chemical Abstracts, (1973), 144672d.

*Primary Examiner*—Delbert R. Phillips
*Assistant Examiner*—Blondel Hazel
*Attorney, Agent, or Firm*—Jon S. Saxe; Jon S. Saxe; Leon S. Bernard

[57] ABSTRACT

The present disclosure relates to dipeptide derivatives. These novel compounds are useful as elastase inhibitors.

34 Claims, No Drawings

DIPEPTIDE DERIVATIVES

BACKGROUND OF THE INVENTION

The use of N-acetyl-L-alanyl-L-prolyl-isopropylamide as an elasterase inhibitor is disclosed in Biochem. 13, 5495 (1974).

DESCRIPTION OF THE INVENTION

The dipeptide derivatives provided by the present invention have the following general formula

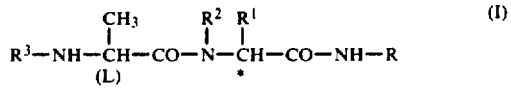

wherein R represents a phenyl, substituted-phenyl, lower cycloalkyl or n-(C$_4$-C$_6$)-alkyl group; R$^1$ and R$^2$ each represent a hydrogen atom or a methyl group, with the proviso that R$^1$ and R$^2$ do not simultaneously represent a hydrogen atom, or R$^1$ and R$^2$ together represent a trimethylene group; R$^3$ represents an acyl group derived from a carboxylic acid, a sulphonic acid or a sulphinic acid; and the asterisk denotes that the configuration at the carbon atom so-marked is L when R$^1$ represents other than a hydrogen atom.

The acyl group denoted by R$^3$ in formula I can represent, for example, an alkanoyl, halo-alkanoyl, nitro-alkanoyl, cyano-alkanoyl, cycloalkylcarbonyl, cycloalkyl-alkanoyl, aroyl, aryl-alkanoyl, alkoxycarbonyl, aryloxycarbonyl, aryl-alkoxycarbonyl, arylsulphonyl, alkylsulphonyl, cycloalkylsulphonyl, cycloalkylsulphinyl, cycloalkyl-alkylsulphonyl or cycloalkyl-alkylsulphinyl group.

The substituted-phenyl group denoted by R in formula I is a phenyl group carrying one or more substituents selected from halogen (i.e. fluorine, chlorine, bromine or iodine), lower alkyl, lower alkoxy, nitro etc. Examples of such substituted-phenyl groups are 4-methoxyphenyl, 4-nitrophenyl, 2,4-dichlorophenyl and the like. The term "lower cycloalkyl" used in relation to R means a monocyclic cycloalkyl group containing from 3 to 8 carbon atoms, i.e. cyclopropyl, cyclobutyl, cyclopentyl, cyclohexyl, cycloheptyl and cyclooctyl. Of the n-(C$_4$-C$_6$)-alkyl groups denoted by R (i.e. n-butyl, n-pentyl and n-hexyl), the n-pentyl group is preferred. The term "alkanoyl" means an alkanoyl group derived from a straight-chain or branched-chain alkanoic acid, preferably a lower alkanoyl group such as acetyl, propionyl, butyryl, isobutyryl, valeroyl, pivaloyl etc. The term "halo-alkanoyl" means an alkanoyl group which carries one or more halogen atoms. The halo-alkanoyl group is preferably a halo-(lower alkanoyl) group such as monochloroacetyl, dichloroacetyl or, especially, trifluoroacetyl. The term "nitro-alkanoyl" means an alkanoyl group carrying a nitro group, preferably a nitro-(lower alkanoyl) group such as nitroacetyl. The term "cyano-alkanoyl" means an alkanoyl group carrying a cyano group, preferably a cyano-(lower alkanoyl) group such as cyanoacetyl. The term "cycloalkylcarbonyl" means a group of the formula R$^5$—CO— in which R$^5$ represents a lower cycloalkyl group as hereinbefore defined (such cycloalkylcarbonyl groups being preferred to hereinafter as lower cycloalkylcarbonyl groups such as cyclopentylcarbonyl, cyclohexylcarbonyl etc) or an aliphatic bridged and/or condensed ring system which may be substituted by oxo or hydroxy (e.g. adamantylcarbonyl etc). The term "cycloalkyl-alkanoyl" means an alkanoyl group in which one of the hydrogen atoms has been replaced by the group R$^5$ hereinbefore (e.g. adamantylacetyl). The term "aroyl" means an aroyl group (e.g. benzoyl) which may carry one or more substituents selected from halogen, lower alkyl, lower alkoxy, nitro, amino, lower alkanoylamino etc. The term "aryl-alkanoyl" means an alkanoyl group in which one of the hydrogen atoms has been replaced by an aryl group, the term "aryl" meaning an aryl group (e.g. phenyl) carrying one or more substituents selected from halogen, lower alkyl, lower alkoxy, nitro, amino, lower alkanoylamino etc). The preferred aryl-alkanoyl groups are the aryl-(lower alkanoyl) groups such as the phenacetyl, phenylpropionyl and like groups. The term "alkoxycarbonyl" means a straight-chain or branched-chain alkoxycarbonyl group, preferably a lower alkoxycarbonyl group such as methoxycarbonyl, ethoxycarbonyl etc. The term "aryloxycarbonyl" means an aryloxycarbonyl group in which the aryl group is as defined earlier. The term "aryl-alkoxycarbonyl" means an alkoxycarbonyl group in which one of the hydrogen atoms has been replaced by an aryl group as defined earlier, preferably an aryl-(lower alkoxycarbonyl) group such as the benzyloxycarbonyl group. The term "arylsulphonyl" means an arylsulphonyl group in which the aryl group is as defined earlier. For example, the arylsulphonyl group may be the benzenesulphonyl group or a naphthalenesulphonyl group (e.g. 1-naphthalenesulphonyl) or a benzenesulphonyl group carrying one or more substituents which may be present on the aforementioned aryl group (e.g. p-toluenesulphonyl, 4-chlorobenzenesulphonyl, 4-aminobenzenesulphonyl, 4-acetylaminobenzenesulphonyl, 4-methoxybenzenesulphonyl, mesitylenesulphonyl etc). The alkylsulphonyl group is preferably a lower alkylsulphonyl group such as methylsulphonyl etc. The term "cycloalkylsulphonyl" means a group of the formula R$^5$—SO$_2$— in which R$^5$ has the significance given earlier, examples of such groups being adamantylsulphonyl (e.g. 1-adamantylsulphonyl), camphorsulphonyl (e.g. D-10-camphorsulphonyl) etc. The term "cycloalkylsulphinyl" means a group of the formula R$^5$—SO— in which R$^5$ has the significance given earlier, examples of such groups being adamantylsulphinyl such as 1-adamantylsulphinyl. The term "cycloalkyl-alkylsulphonyl" means an alkylsulphonyl group which carries a substituent R$^5$ hereinbefore (e.g. isobornylmethylsulphonyl etc) and the term "cycloalkyl-alkylsulphinyl" means an alkylsulphinyl group which carries a substituent R$^5$ hereinbefore (e.g. bornylmethylsulphinyl etc). The terms "lower alkanoyl", "lower alkyl" and "lower alkoxy" as used herein, alone or in combination as the context may require, mean that such groups preferably contain up to 6 carbon atoms. Examples of lower alkyl and lower alkoxy groups which, like the lower alkanoyl groups, can be straight-chain or branched-chain, are methyl, ethyl, propyl, isopropyl etc, and methoxy, ethoxy, propoxy, isopropoxy etc, respectively.

In one particular embodiment of the present invention, R$^3$ represents the trifluoroacetyl group or a lower alkanoyl, lower cycloalkylcarbonyl, benzoyl, phenyl-(lower alkanoyl), lower alkoxycarbonyl, phenoxycarbonyl, phenyl-(lower alkoxycarbonyl), benzenesulphonyl, naphthalenesulphonyl or lower alkylsulphonyl group, the benzoyl, phenoxycarbonyl and benzenesulphonyl groups and the phenyl portion of the phenyl-(lower alkanoyl) and phenyl-(lower alkoxycarbonyl) groups optionally carrying one or more substituents selected from halogen, lower alkyl, lower alkoxy and nitro.

In another particular embodiment of the present invention, $R^3$ represents a lower alkanoyl, lower cycloalkylcarbonyl, benzoyl, phenyl-(lower alkanoyl), lower alkoxycarbonyl, phenoxycarbonyl or phenyl-(lower alkoxycarbonyl) group, the benzoyl and phenoxycarbonyl groups and the phenyl portion of the phenyl-(lower alkanoyl) and phenyl-(lower alkoxycarbonyl) groups optionally carrying one or more substituents selected from halogen, lower alkyl, lower alkoxy and nitro.

One preferred class of dipeptide derivatives provided by the present invention comprises those in which $R^1$ represents a hydrogen atom and $R^2$ represents a methyl group or $R^1$ and $R^2$ together represent a trimethylene group. Another preferred class of dipeptide derivative provided by the invention comprises those in which $R^3$ represents an alkanoyl group, especially a lower alkanoyl group and particularly propionyl, an aroyl group, especially benzoyl, an aryl-alkoxycarbonyl group, especially an aryl-(lower alkoxycarbonyl) group and particularly benzyloxycarbonyl, or an arylsulphonyl group, especially p-toluenesulphonyl. Other preferred values for $R^3$ are the cycloalkylsulphonyl, cycloalkylsulphinyl, cycloalkyl-alkylsulphonyl and cycloalkyl-alkylsulphinyl groups. When R represents a substituted-phenyl group, this is preferably a 4-methoxyphenyl, 4-nitrophenyl or 2,4-dichlorophenyl group. When R represents a lower cycloalkyl group, this is preferably a cycloalkyl group containing from 5 to 8 carbon atoms.

Examples of dipeptide derivatives of formula I are:
N-Benzyloxycarbonyl-L-alanyl-L-propline anilide,
N-benzyloxycarbonyl-L-alanyl-L-proline 2,4-dichloroanilide,
N-benzyloxycarbonyl-L-alanyl-L-proline 4-nitroanilide,
N-benzyloxycarbonyl-L-alanyl-L-proline 4-methoxyanilide,
N-acetyl-L-alanyl-L-proline anilide,
N-propionyl-L-alanyl-L-proline anilide,
N-benzoyl-L-alanyl-L-proline anilide,
N-pivaloyl-L-alanyl-L-proline anilide,
N-hexanoyl-L-alanyl-L-proline anilide,
N-trifluoroacetyl-L-alanyl-L-proline anilide,
N-cyanoacetyl-L-alanyl-L-proline anilide,
N-(1-adamantylcarbonyl)-L-alanyl-L-proline anilide,
N-(1-adamantylacetyl)-L-alanyl-L-proline anilide,
N-(p-toluenesulphonyl)-L-alanyl-L-proline anilide,
N-benzenesulphonyl-L-alanyl-L-proline anilide,
N-(4-nitrobenzenesulphonyl)-L-alanyl-L-proline anilide,
N-(1-naphthalenesulphonyl)-L-alanyl-L-proline anilide,
N-(1-adamantylsulphinyl)-L-alanyl-L-proline anilide,
N-(1-adamantylsulphonyl)-L-alanyl-L-proline anilide,
N-(D-10-camphorsulphonyl)-L-alanyl-L-proline anilide,
N-(4-acetylaminobenzenesulphonyl)-L-alanyl-L-proline anilide,
N-(4-methoxybenzenesulphonyl)-L-alanyl-L-proline anilide,
N-mesitylenesulphonyl-L-alanyl-L-proline anilide,
N-propionyl-L-alanyl-L-proline 2,4-dichloroanilide,
N-propionyl-L-alanyl-L-proline 4-nitroanilide,
N-propionyl-L-alanyl-L-proline 4-methoxyanilide,
N-benzyloxycarbonyl-L-alanyl-L-proline cyclopentylamide,
N-benzyloxycarbonyl-L-alanyl-L-proline cyclohexylamide,
N-benzyloxycarbonyl-L-alanyl-L-proline cycloheptylamide,
N-benzyloxycarbonyl-L-alanyl-L-proline cyclooctylamide,
N-propionyl-L-alanyl-L-proline cyclopentylamide,
N-propionyl-L-alanyl-L-proline cyclohexylamide,
N-(p-toluenesulphonyl)-L-alanyl-L-proline cyclohexylamide,
N-propionyl-L-alanyl-L-proline cycloheptylamide,
N-propionyl-L-alanyl-L-proline cyclooctylamide,
N-benzyloxycarbonyl-L-alanyl-L-alanine anilide,
N-propionyl-L-alanyl-L-alanine anilide,
N-benzoyl-L-alanyl-L-alanine anilide,
N-benzyloxycarbonyl-L-alanyl-L-alanine cyclohexylamide,
N-propionyl-L-alanyl-L-alanine cyclohexylamide,
N-benzyloxycarbonyl-L-alanyl-L-proline n-pentylamide and
N-propionyl-L-alanyl-L-proline n-pentylamide.

According to the process provided by the present invention the dipeptide derivatives aforesaid are manufactured by (a) condensing an amide of the general formula

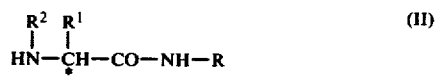

wherein R, $R^1$, $R^2$ and the asterisk have the significance given earlier, with an N-protected-L-alanine of the general formula

wherein $R^4$ represents a protecting group which is known per se in peptide chemistry, or (b) amidating a carboxylic acid of the general formula

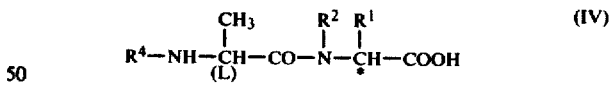

wherein $R^1$, $R^2$, $R^4$ and the asterisk have the significance given earlier, and, in either case and where required, cleaving off the protecting group denoted by $R^4$ and introducing a group denoted by $R^3$ hereinbefore in accordance with methods known per se and, if desired, oxidising a resulting dipeptide derivative of formula I in which $R^3$ represents an acyl group derived from a sulphinic acid to give a corresponding dipeptide derivative of formula I in which $R^3$ represents an acyl group derived from a sulphonic acid.

The protecting group denoted by $R^4$ in the N-protected-L-alanine starting materials of formula III and the carboxylic acid starting materials of formula IV can be any protecting group known per se in peptide chemistry. Thus, for example, $R^4$ can represent the trifluoroacetyl or p-toluenesulphonyl group or a lower alkoxycarbonyl group (e.g. tert.butoxycarbonyl etc), an aryloxycarbonyl group (e.g. phenoxycarbonyl etc) or an aryl-(lower alkoxycarbonyl) group (e.g. benzyloxycarbonyl etc). $R^4$ may also represent, for example, a formyl, trityl, 2-(biphenylyl)-isopropyloxycarbonyl or phthaloyl group. In a preferred embodiment of this invention, $R^4$ represents an aryl-(lower alkoxycarbonyl) group, especially the benzyloxycarbonyl group.

The condensation of an amide of formula II with an N-protected-L-alanine of formula III in accordance with embodiment (a) of the present process can be carried out according to methods which are known per se in peptide chemistry; for example, according to the mixed anhydride, azide, activated ester or acid chloride method.

For example, an amide of formula II can be condensed with an N-protected-L-alanine of formula III in which the carboxyl group is present in the form of a mixed anhydride residue formed with an inorganic acid. Suitably, such an N-protected-L-alanine carrying a free carboxyl function is treated with a tertiary base such as a tri(lower alkyl)amine (e.g. triethylamine) or N-ethylmorpholine in an inert organic solvent (e.g. tetrahydrofuran, 1,2-dimethoxyethane, dichloromethane, toluene, petroleum ether or mixtures thereof) and the salt obtained is reacted with a chloroformate (e.g. ethyl chloroformate or isobutyl chloroformate) at a low temperature. The mixed anhydride obtained is then conveniently condensed in situ with an amide of formula II.

Again, for example, an amide of formula II can be condensed with an N-protected-L-alanine in which the carboxyl group is in the form of an acid azide. This condensation is expediently carried out in the presence of an inert organic solvent such as dimethylformamide or ethyl acetate at a low temperature.

Yet again, for example, an amide of formula II can be condensed with an N-protected-L-alanine in which the carboxyl group is in the form of an active ester group (e.g. the p-nitrophenyl, 2,4,5-trichlorophenyl, N-hydroxysuccinimide or hydroxybenztriazole ester group). This condensation is suitably carried out in an inert organic solvent such as dimethylformamide, tetrahydrofuran etc.

Further, for example, an amide of formula II can be condensed with an N-protected-L-alanine in the presence of dicyclohexylcarbodiimide. This condensation is expediently carried out in the presence of an inert organic solvent (e.g. dimethylformamide or methylene chloride) at a low temperature (e.g. 0° C.).

Still further, for example, an amide of formula II can be condensed with an N-protected-L-alanine in which the carboxyl group is in the form of an acid chloride. It is preferred to carry out this condensation in the presence of a base (e.g. an alkali metal hydroxide such as sodium hydroxide) and at a low temperature (e.g. 0° C.).

The amidation of a carboxylic acid of formula IV in accordance with embodiment (b) of the present process can be carried out according to methods known per se. Thus, for example, a carboxylic acid of formula IV in which $R^2$ represents a methyl group or $R^1$ and $R^2$ together represent a trimethylene group can be converted in the manner described earlier in connection with the condensation of an amide of formula II with an N-protected-N-alanine of formula III into an acid azide, activated ester, mixed anhydride or acid chloride as the case may require and can then be reacted with an appropriate amine yielding the group denoted by R hereinbefore. Alternatively, a carboxylic acid of formula IV in which $R^2$ represents a methyl group or $R^1$ and $R^2$ together represent a trimethylene group can be amidated in the presence of dicyclohexylcarbodiimide. In the amidation of a carboxylic acid of formula IV in which $R^2$ represents a hydrogen atom, care must be taken that no racemisation occurs. This latter amidation can suitably be carried out according to the acid azide or N-hydroxysuccinimide/dicyclohexylcarbodiimide method.

The condensation of an amide of formula II with an N-protected-L-alanine of formula III or the amidation of a carboxylic acid of formula IV yields a compound of the general formula

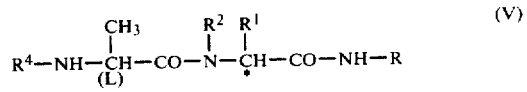

(V)

wherein R, $R^1$, $R^2$, $R^4$ and the asterisk have the significance given earlier.

It will be appreciated that compounds of formula V in which the protecting group denoted by $R^4$ is the trifluoroacetyl or p-toluenesulphonyl group or a lower alkoxycarbonyl, aryloxycarbonyl or aryl-(lower alkoxycarbonyl) group correspond to dipeptide derivatives of formula I in which $R^3$ has any of these values.

The protecting group denoted by $R^4$ can be cleaved off from a compound of formula V according to known methods. For example, the cleavage of the trifluoroacetyl group can be carried out by treatment with an appropriate base (e.g. an alkali metal hydroxide such as sodium hydroxide). The p-toluenesulphonyl group can be cleaved off by treatment with an alkali metal (e.g. sodium) in liquid ammonia. The cleavage of a lower alkoxycarbonyl, aryloxycarbonyl or aryl-(lower alkoxycarbonyl) group or the 2-(biphenylyl)-isopropyloxycarbonyl group can be carried out by hydrolysis (e.g. by treatment with hydrogen bromide in glacial acetic acid). An aryl-(lower alkoxycarbonyl) group can also be cleaved off by hydrogenolysis (e.g. in the presence of palladium-on-charcoal or platinum oxide). The tert-butoxycarbonyl or 2-(biphenylyl)-isopropyloxycarbonyl group may also be cleaved off using hydroge chloride in dioxan or trifluoroacetic acid.

The cleavage of the protecting group denoted by $R^4$ from a compound of formula V yields a compound of the general formula

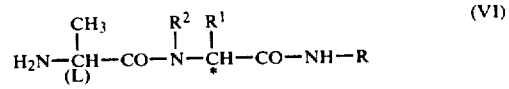

(VI)

wherein R, $R^1$, $R^2$ and the asterisk have the significance given earlier, which may be isolated if desired, suitably in the form of a hydrohalide salt such as the hydrobromide, and then converted into a depeptide derivative of formula I by the introduction of the group $R^3$ according to methods known per se or which may be converted in situ into a dipeptide derivative of formula I in the same manner.

The introduction of a group denoted by $R^3$ into a compound of formula VI is carried out in accordance with methods which are known per se.

Thus, for example, in one method, a compound of formula VI can be treated with an appropriate acid chloride (e.g. an alkanoic acid chloride such as pivaloyl chloride, a cycloalkane carboxylic acid chloride such as cyclohexane carboxylic acid chloride, a cycloalkyl-alkanoic acid chloride such as adamantylacetyl chloride, an aroic acid chloride such as benzoyl chloride an aryl-alkanoic acid chloride such as phenacetyl chloride, an arylsulphonic acid chloride such as p-toluenesulphonyl chloride, benzenesulphonyl chloride, 4-nitrobenzenesulphonyl chloride or 1-naphthalenesulphonyl chloride, an alkanesulphonic acid chloride such as methanesulphonyl chloride, a cycloalkanesulphinyl chloride such as adamantanesulphinyl chloride or the like) in the presence of a base (e.g. an alkali metal hydroxide such as sodium hydroxide or a tertiary amine such as triethylamine or pyridine). This treatment is advantageously carried out at about room temperature. It is advantageous to carry out this treatment in the presence of an inert organic solvent such as a halogenated hydrocarbon (e.g. methylene chloride) when an alkali metal hydroxide is used as the base. When a tertiary amine is used as the base, it can be present in excess and can thereby also serve as a solvent.

In another method, for example, a compound of formula VI can be treated with an appropriate acid anhydride (e.g. a halo-alkanoic acid anhydride such as trifluoroacetic anhydride or an alkanoic acid anhydride such as propionic anhydride, isobutyric anhydride or n-valeric anhydride) in the presence of a base, preferably a tertiary amine and, in particular, pyridine. It is expedient to carry out this treatment at about room temperature. An excess of the tertiary amine can be present and can thereby also serve as a solvent. This treatment can, however, also be carried out in the presence of an appropriate inert organic solvent.

In a further method, for example, a compound of formula VI can be treated with an appropriate chloroformate in the presence of N-ethylmorpholine. Examples of chloroformates which may be used in this method are the alkyl chloroformates, particularly ethyl chloroformate and isobutyl chloroformate. This treatment may be carried out in an inert organic solvent (e.g. tetrahydrofuran) and at a temperature of about room temperature.

In yet a further method, a hydrohalide salt, particularly the hydrobromide salt, of a compound of formula VI can be condensed with an appropriate acid yielding the group denoted by $R^3$ in the presence of a suitable condensing agent such as a carbodiimide (e.g. N,N-dicyclohexylcarbodiimide) in accordance with known procedures. The condensation is carried out in the presence of a tertiary amine (e.g. triethylamine or N-ethylmorpholine) and preferably in the presence of an inert organic solvent such as a chlorinated hydrocarbon (e.g. methylene chloride). It is expedient to carry out the condensation at about 0° C.

The oxidation of a dipeptide derivative of formula I in which $R^3$ represents an acyl group derived from a sulphinic acid to give a corresponding dipeptide derivative of formula I in which $R^3$ represents an acyl group derived from a sulphonic acid can be carried out in accordance with methods known per se. Suitable oxidising agents which can be used include potassium permanganate in acetone and organic peracids such as peracetic acid, perbenzoic acid etc. The organic peracid may be formed in situ using hydrogen peroxide and the corresponding organic acid (e.g. hydrogen peroxide and glacial acetic acid). The oxidation is expediently carried out at about room temperature, but in certain circumstances it can be advantageous to warm the oxidation mixture (e.g. up to about 65° C.).

The amide starting materials of formula II can be prepared for example, by amidating a corresponding N-protected α-amino carboxylic acid in a manner analogous to that described earlier in connection with the amidation of a carboxylic acid of formula IV and subsequently removing the N-protecting group in a manner analogous to that described earlier in connection with the cleavage of the protecting group $R^4$ from a compound of formula VI.

The N-protected-L-alanine starting materials of formula III are known compounds which can be prepared according to conventional methods from L-alanine.

The starting materials of formula IV can be prepared, for example, by condensing an N-protected-L-alanine with a lower alkyl or aryl-(lower alkyl) ester of L-alanine, L-proline, N-methyl-L-alanine or sarcosine in accordance with methods known per se (e.g. the mixed anhydride, azide, activated ester or acid chloride method described earlier in connection with the condensation of an amide of formula II with an N-protected-L-alanine of formula III) and then hydrolysing a resulting ester to the corresponding carboxylic acid.

The dipeptide derivatives of formula I hereinbefore possess activity as elastase inhibitors.

Thus, for example, the present dipeptide derivatives possess in vitro elastase inhibiting activity against human granulocyte elastase. This activity can be demonstrated according to the test method of Visser L. and Blout E. R., Biochem. Biophys. Acta 268 (1972) 257, using human granulocyte elastase as the enzyme. The results obtained with representative dipeptide derivatives of formula I in this test are given in Table I hereinafter, the $I_{50}$ being the concentration in millimoles per liter which gives 50% inhibition of the human granulocyte elastase:

Table I

| Dipeptide derivative | $I_{50}$ |
|---|---|
| (N-Hexanoyl-L-alanyl-L-proline) anilide | 0.8 |
| N-Benzyloxycarbonyl-L-alanyl-L-proline cyclohexylamide | 1.0 |
| N-Benzylcarbonyl-L-alanyl-L-proline n-pentylamide | ca 5.0 |
| N-(p-Toluenesulphonyl)-L-alanyl-L-proline anilide | 0.06 |
| N-(l-Adamantylcarbonyl)-L-alanyl-L-proline anilide | 0.6 |
| N-(l-Adamantylacetyl)-L-alanyl-L-proline anilide | 0.06 |
| N-(l-Adamantylsulphonyl)-L-alanyl-L-proline anilide | 0.007 |

Again, for example, the dipeptide derivative of formula I in which $R^3$ represents an acetyl, trifluoroacetyl or propionyl group possess in vitro elastase inhibiting activity against porcine pancreatic elastase. This activity can be demonstrated according to the aforementioned test method using porcine pancreatic elastase as the enzyme. The results obtained with representative dipeptide derivatives are given in Table II hereinafter, the $K_i$ being the inhibitor constant in millimoles per liter:

Table II

| Dipeptide derivative | $K_i$ (mmol/liter) |
|---|---|
| N-Propionyl-L-alanyl-L-proline anilide | 0.04 |
| N-Propionyl-L-alanyl-L-proline 4-nitroanilide | 0.026 |
| N-Propionyl-L-alanyl-L-proline cyclohexylamide | 0.02 |
| N-Propionyl-L-alanyl-L-alanine anilide | 0.04 |
| N-Trifluoroacetyl-L-alanyl-L-proline anilide | 0.0014 |

The in vivo elastase inhibiting activity of dipeptide derivatives of formula I in which $R^3$ represents an acetyl, trifluoroacetyl or propionyl group can be demonstrated, for example, by administering said dipeptide derivatives orally or intraperitoneally to rats in which an oedema has previously been induced in a hind paw by the subcutaneous injection therein of a proteolytic enzyme such as porcine pancreatic elastase. Following such oral or parenteral administration, the size of the oedema is reduced.

The dipeptide derivatives of formula I hereinbefore may be used in the treatment of degenerative diseases associated with the action of elastase-like enzymes such as emphysema and arthritis. They may also be used for the treatment of inflammatory conditions in which elastase-like enzymes act as mediators of inflammation. Further, they may be used as adjuncts to topical antifungal and antibacterial preparations for the treatment of infections associated with the breakdown of host-elastic tissue.

The dipeptide derivatives of formula I hereinbefore may be used as medicaments in the form of pharmaceutical preparations which contain them in association with a compatible pharmaceutical carrier material. This carrier material may be an inorganic or inorganic inert carrier material suitable for enteral (e.g. oral) or parenteral administration. Examples of such carrier materials include water, lactose, starch, magnesium stearate, talc, gum arabic, gelatin, polyalkyleneglycols, petroleum jelly etc. The pharmaceutical preparations can be made up in a solid form (e.g. as tablets, dragees, suppositories or capsules) or in a liquid form (e.g. as solutions, emulsions, suspensions or aerosols). The pharmaceutical preparations may be subjected to customary pharmaceutical operations such as sterilisation and may contain adjuvants such as preserving agents, stabilising agents, wetting agents, salts for varying the osmotic pressure etc.

The dipeptide derivatives provided by the present invention can be expediently administered in a dosage range of from about 5 mg to 30 mg, preferably 10 mg, per day. It will, of course, be appreciated that this dosage range is given by way of example only and that it can be varied upwards or downwards depending on factors such as the particular dipeptide derivative to be administered, the particular condition to be treated and the individual requirements of the patient as determined by the attending physician.

The following Examples illustrate the process provided by the present invention. In the Examples the term "ether" means diethyl ether.

EXAMPLE 1

(A) The preparation of the starting material:
(i) N-Benzyloxycarbonyl-L-alanine anilide 11.15 g (0.05 mol) of N-benzyloxycarbonyl-L-alanine were dissolved in 75 ml of dry tetrahydrofuran and the mixture was cooled to −10° C. 6.35 ml (0.05 mol) of N-ethylmorpholine were added followed by 6.5 ml of isobutyl chloroformate and the resulting solution was stirred at −10° C. for 20 minutes. 4.65 ml (0.05 mol) of aniline were then added, the mixture was stirred at 0° C. for 1 hour and then left to stand at room temperature for 3 hours. The solvents were removed by evaporation and the residue was dissolved in 200 ml of chloroform. The solution was washed with 150 ml of 1-N hydrochloric acid, 150 ml of water and 150 ml of 5% sodium bicarbonate solution, dried over magnesium sulphate and evaporated to give a white solid. This solid was treated with 300 ml of petroleum ether to yield 11.89 g (80%) of N-benzyloxycarbonyl-L-alanine anilide of melting point 161°–163° C.

Analysis for $C_{17}H_{18}O_3N_2$ (298.34): Calculated: C: 68.44; H: 6.08; N: 9.39. Found: C: 68.31; H: 5.96; N: 9.42.

(ii) L-Alanine anilide hydrobromide 6 g (0.02 mol) of N-benzyloxycarbonyl-L-alanine anilide were dissolved in 30 ml of 4-N hydrogen bromide in acetic acid and the solution was stirred for 1 hour at room temperature. 300 ml of dry ether were then added. An oil precipitated out and was allowed to settle. The solvents were decanted off and the oil was washed with two 150 ml portions of ether, dissolved in a small amount of methanol and an excess of ethyl acetate was added. The product crystallised out, there being obtained 4.0 g (81%) of L-alanine anilide hydrobromide of melting point 244°–247° C.

(B) The process:
(i) N-Benzyloxycarbonyl-L-alanyl-L-alanine anilide 4.35 g (0.019 mol) of N-benzyloxycarbonyl-L-alanine were dissolved in 40 ml of dry tetrahydrofuran and the solution was cooled to −10° C. 2.47 ml (0.019 mol) of N-ethylmorpholine were added followed by 2.56 ml (0.019 mol) of isobutyl chloroformate and the resulting solution was stirred at −10° C. for 20 minutes.

4.95 g (0.019 mol) of L-alanine anilide hydrobromide were dissolved in 40 ml of dry dimethylformamide, the solution was cooled to 0° C. and 2.47 ml (0.019 mol) of N-ethylmorpholine were added. This solution was then combined with the mixed anhydride solution prepared as described in the preceding paragraph, stirred at 0° C. for 1 hour and then left to stand at room temperature for 16 hours. The solvents were removed by evaporation to give a white solid which was recrystallised from ethanol to yield 4.9 g (67%) of N-benzyloxycarbonyl-L-alanyl-L-alanine anilide of melting point 219°–221° C.

(ii) L-Alanyl-L-alanine anilide hydrobromide 5.5 g (0.0149 g) of N-benzyloxycarbonyl-L-alanyl-L-alanine anilide were dissolved in 30 ml of 4-N hydrogen bromide in acetic acid and the solution was stirred at room temperature for 1 hour. 300 ml of dry ether were then added. A white solid separated out and was allowed to settle. The solution was decanted off and the solid washed with two 150 ml portions of ether. Recrystallisation of the solid from methanol/ethyl acetate yielded 4.1 g (88%) of L-alanyl-L-alanine anilide hydrobromide.

(iii) N-Benzoyl-L-alanyl-L-alanine anilide 4.1 g (0.013 mol) of L-alanyl-L-alanine anilide hydrobromide were dissolved in 120 ml of dry pyridine and 3 ml (0.026 mol) of benzoyl chloride were added. The solution was stirred at room temperature for 3 hours and was then evaporated to yield a solid. 50 ml of water were added, the solid was filtered off, washed with 50 ml of water and then recrystallise from ethanol to yield 3.15 g (72%) of N-benzoyl-L-alanyl-L-alanine anilide of melting point 245°–248° C.; $[\alpha]_D^{20} = +66.6°$ (c = 1.086% in dimethylformamide).

Analysis for $C_{19}H_{21}O_3N_3$ (339.40): Calculated: C: 67.24; H: 6.24; N: 12.38. Found: C: 67.33; H: 6.30; N: 12.43.

(iv) N-Propionyl-L-alanyl-L-alanine anilide 3.8 g (0.012 mol) of L-alanyl-L-alanine anilide hydrobromide were dissolved in 80 ml of dry pyridine and 3.4 ml (0.024 mol) of propionic anhydride were added. The solution was stirred at room temperature for 2 hours and then evaporated to give a solid. This solid was recrystallised from ethanol and then from methanol to yield 1.9 g (54%) of N-propionyl-L-alanyl-L-alanine anilide of melting point 281°-284° C.; $[\alpha]_D^{20} = -101.1°$ (c=0.995% in acetic acid).

EXAMPLE 2

(A) The preparation of the starting material:

(i) N-Benzyloxycarbonyl-L-alanine cyclohexylamide 11.15 g (0.05 mol) of N-benzyloxycarbonyl-L-alanine were dissolved in 75 ml of dry tetrahydrofuran and the mixture was cooled to −10° C. 6.35 ml (0.05 mol) of N-ethylmorpholine were added followed by 6.5 ml of isobutyl chloroformate and the solution obtained was stirred at −10° C. for 20 minutes. A solution of 6.05 ml of cyclohexylamine in 75 ml of tetrahydrofuran was then added and the resulting solution was stirred at 0° C. After 30 minutes the mixture solidified and 30 ml of dimethylformamide were added. After stirring for a further 1 hour at 0° C., the solvent was removed by evaporation, water was added and the solid filtered off. The solid was washed with 150 ml of 1-N hydrochloric acid, 150 ml of water, 150 ml of 5% sodium bicarbonate solution and 150 ml of water and then dried in vacuo. Recrystallisation from ethyl acetate yielded 11.7 g (77%) of N-benzyloxycarbonyl-L-alanine cyclohexylamide of melting point 163°-164° C.

Analysis for $C_{17}H_{24}O_3N_2$ (304.39): Calculated: C: 67.08; H: 7.95; N: 9.20. Found: C: 66.83; H: 7.89; N: 9.14.

(ii) L-Alanyl-L-alanine cyclohexylamide hydrobromide 7.0 g of N-benzyloxycarbonyl-L-alanine cyclohexylamide were treated with hydrogen bromide in acetic acid in an analogous manner to that described in Example 1(A)(ii). The L-alanyl-L-alanine cyclohexylamide was obtained in the form of an oil after working-up the mixture in the manner described in Example 1(A)(ii).

(B) The process:

(i) N-Benzyloxycarbonyl-L-alanyl-L-alanine cyclohexylamide 5.14 g of N-benzyloxycarbonyl-L-alanine were dissolved in 40 ml of dry tetrahydrofuran and the solution was cooled to −10° C. 2.92 ml of N-ethylmorpholine were added followed by 3.01 ml of isobutyl chloroformate. The solution obtained was then stirred at −10° C. for 20 minutes.

The oil obtained according to part (A)(ii) of this Example was dissolved in 40 ml of dry dimethylformamide, the solution was cooled to 0° C. and 2.92 ml of N-ethylmorpholine were added. This solution was then combined with the mixed anhydride solution prepared as described in the preceding paragraph. After stirring at 0° C. for 15 minutes the mixture solidified and 30 ml of dimethylformamide were added. The product did not dissolve completely and the mixture was left to stand for 72 hours. Water was added to the suspension, the product was filtered off, washed with ether and dried. There were obtained 5.8 g (67%) of N-benzyloxycarbonyl-L-alanyl-L-alanine cyclohexylamide of melting point 233°-234° C.; $[\alpha]_D^{20} = -4.5°$ (c=0.9512% in dimethylformamide).

Analysis for $C_{20}H_{29}O_4N_3$ (375.47): Calculated: C: 63.98; H: 7.79; N: 11.19. Found: C: 64.14; H: 7.82; N: 11.51.

(ii) L-Alanyl-L-alanine cyclohexylamide hydrobromide 3.0 g of N-benzyloxycarbonyl-L-alanyl-L-alanine cyclohexylamide were treated with hydrogen bromide in acetic acid in a manner analogous to that described in Example 1(B)(ii) to give L-alanyl-L-alanine cyclohexylamide hydrobromide in the form of an oil.

(iii) N-Propionyl-L-alanyl-L-alanine cyclohexylamide

The oil obtained according to part (B)(ii) of this Example was dissolved in 50 ml of dry pyridine and treated with 2.1 ml of propionic anhydride. The mixture was then stirred at room temperature for 2 hours. The mixture was evaporated and the crystalline residue recrystallised from methanol. There were obtained 1.84 g (78%) of N-propionyl-L-alanyl-L-alanine cyclohexylamide of melting point 299°-300° C.; $[\alpha]_D^{20} = -81.1°$ (c=1.0424% in glacial acetic acid).

Analysis for $C_{15}H_{27}O_3N_3$ (297.4): Calculated: C: 60.58; H: 9.15; N: 14.13. Found: C: 60.63; H: 9.15; N: 14.07.

EXAMPLE 3

(A) The preparation of the starting material:

N-Benzyloxycarbonyl-L-alanyl-L-proline 289 g (0.903 mol) of N-benzyloxycarbonyl-L-alanine N-hydroxysuccinimide ester were dissolved in 1800 ml of 1,2-dimethoxyethane and to this solution was added a solution of 103.98 g (0.903 mol) of L-proline in 1350 ml of water followed by 267 ml (1.8 mol) of triethylamine. The mixture was stirred for 16 hours at room temperature and then the dimethoxyethane was removed by evaporation. The aqueous solution was then extracted twice with 300 ml of ethyl acetate each time and the organic layers were discarded. The remaining solution was acidified to pH 1-2 using concentrated hydrochloric acid and extracted twice with 900 ml of ethyl acetate each time. The organic layers were combined and washed twice with 400 ml of water each time, then dried over sodium sulphate, filtered and evaporated to an oil. On trituration with 1600 ml of ether, the product crystallised out and was filtered off, washed with ether and dried to yield 193.8 g of N-benzyloxycarbonyl-L-alanyl-L-proline of melting point 124°-125° C. A second crop of 27.6 g (melting point 123°-124° C.) was obtained by evaporation of the mother liquors, trituration with 300 ml of ether and storage at 4° C. for 1 hour; total yield 77%; $[\alpha]_D^{20} = -91.2°$ (c=1.03% in methanol).

Analysis for $C_{16}H_{20}O_5N_2$ (320.35): Calculated: C: 60.00; H: 6.29; N: 8.74. Found: C: 59.91; H: 6.40; N: 8.85.

(B) The process:

(i) N-Benzyloxycarbonyl-L-alanyl-L-proline 2,4-dichloroanilide 3.2 g (0.01 mol) of N-benzyloxycarbonyl-L-alanyl-L-proline were dissolved in 50 ml of dry tetrahydrofuran and the solution was cooled to −10° C. 1.27 ml (0.01 mol) of N-ethylmorpholine were added followed by 1.31 ml (0.01 mol) of isobutyl chloroformate and the mixture was stirred at −10° C. for 20 minutes. 1.62 g (0.01 mol) of 2,4-dichloroaniline were then added to give a dark brown solution which was then stirred at 0° C. for 1 hour and left to stand at room temperature for 72 hours. The solution was evaporated, the residue dissolved in 100 ml of chloroform and washed with 80 ml of 1-N-hydrochloric acid, 80 ml of water and 80 ml of 5% sodium bicarbonate solution. The organic phase was dried over magnesium sulphate and evaporated to give a brown oil. Crystallization from ethyl acetate/ether gave 2.03 g of N-benzyloxycarbonyl-L-alanyl-L-proline 2,4-dichloroanilide of melting point 136°-137° C.; $[\alpha]_D^{20} = -151.1°$ (c=1.144% in methanol). A further 1.03 g of melting point 136°-137° C. was obtained by evaporating the mother liquor and crystallising the oil obtained from a smaller volume of ethyl acetate/ether. The total yield was 66%.

Analysis for $C_{22}H_{23}O_4N_3Cl_2$ (464.36): Calculated: C: 56.91; H: 5.00; N: 9.05. Found: C: 56.79; H: 5.02; N: 9.10.

(ii) N-Propionyl-L-alanyl-L-proline 2,4-dichloroanilide 2.54 g (0.0055 mol) of N-benzyloxycarbonyl-L-alanyl-L-proline 2,4-dichloroanilide were dissolved in 10 ml of 4-N hydrogen bromide in acetic acid and the solution was stirred for 1 hour to give a dark blue solution. Upon addition of 100 ml of dry ether an oil precipitated. This oil was allowed to settle, the liquids were decanted off and the oil was washed with 100 ml of ether. The oil was then dissolved in 30 ml of dry pyridine and 1.42 ml (0.011 mol) of propionic anhydride were added to the solution. The purple-coloured solution was stirred at room temperature for 2 hours and then evaporated. The final traces of pyridine were removed by the addition of 50 ml of toluene and re-evaporation. The residue was dissolved in 100 ml of chloroform and the solution washed with 80 ml of 1-N hydrochloric acid, 80 ml of water and 80 ml of 5% sodium bicarbonate solution, dried over magnesium sulphate and evaporated to give an oil. This oil was treated with 40 ml of ethyl acetate and left to stand at 4° C. for 16 hours. There was obtained a crystalline solid which was recrystallised from warm ethyl acetate/petroleum ether to give 0.59 g (28%) of N-propionyl-L-alanyl-L-proline 2,4-dichloroanilide of melting point 136.5°–138° C.; $[\alpha]_D^{20} = -174.8°$ (c = 0.992% in methanol).

Analysis for $C_{17}H_{21}O_3N_3Cl_2$ (386.29): Calculated: C: 52.86; H: 5.48; N: 10.88. Found: C: 52.90; H: 5.67; N: 10.85.

EXAMPLE 4

(A) The preparation of the starting material:
N-Benzyloxycarbonyl-L-alanyl-L-proline This compound was prepared as described in Example 3(A).

(B) The process:

(i) N-Benzyloxycarbonyl-L-alanyl-L-proline anilide 32 g (0.1 mol) of N-benzyloxycarbonyl-L-alanyl-L-proline were dissolved in 300 ml of dry tetrahydrofuran and the solution was cooled to −10° C. 12.7 ml (0.1 mol) of N-ethylmorpholine and 13.1 ml (0.1 mol) of isobutyl chloroformate were added and the solution was stirred for 20 minutes while maintaining the temperature at −10° C. 9.3 ml of aniline were then added and the mixture was stirred at 0° C. for 1 hour. The mixture was found to be slightly acidic and a further 1 g of N-ethylmorpholine was added. The solution was then left to stand at room temperature for 16 hours. The solution was evaporated, there being obtained a white crystalline solid which was treated with 500 ml of ether, filtered, washed and dried to give 31.8 g of N-benzyloxycarbonyl-L-alanyl-L-proline anilide of melting point 139.5°–140.5° C.; $[\alpha]_D^{20} = -125.5°$ (c = 1.195% in methanol). A second crop (1.4 g; melting point 138°–139° C.) was obtained by evaporating the mother liquor to a small volume, when crystallisation took place. The total yield was 81%.

Analysis for $C_{22}H_{25}O_4N_3$ (395.46): Calculated: C: 66.82; H: 6.37; N: 10.62. Found: C: 66.64; H: 6.50; N: 10.44.

(ii) L-Alanyl-L-proline anilide hydrobromide 10 g (0.025 mol) of N-benzyloxycarbonyl-L-alanyl-L-proline anilide were dissolved in 50 ml of 4-N hydrogen bromide in acetic acid and the solution was stirred at room temperature for 1 hour. 300 ml of dry ether were then added. An oil precipitated out and was allowed to settle. The solution was decanted off and the oil was washed with two 150 ml portions of ether, dissolved in the minimum volume of methanol and treated with an excess of ethyl acetate. The product soon crystallised, there being obtained 7.2 g (83%) of L-alanyl-L-proline anilide hydrobromide of melting point 211°–214° C.

(iii) N-Acetyl-L-alanyl-L-proline anilide 2 g (0.00585 mol) of L-alanyl-L-proline anilide hydrobromide were dissolved in 40 ml of dry pyridine and 1.1 ml (0.0117 mol) of acetic anhydride were added. The solution was stirred at room temperature for 1 hour and then evaporated. Final traces of pyridine were removed by addition of 20 ml of toluene ane re-evaporation. The residue was dissolved in 100 ml of chloroform and the solution washed with 80 ml of saturated sodium chloride solution, dried over magnesium sulphate and evaporated to an oil. This oil crystallised from ethyl acetate/petroleum ether to give 1.64 g (93%) of N-acetyl-L-alanyl-L-proline anilide of melting point 163°–165° C.; $[\alpha]_D^{20} = -186.2°$ (c = 1.022% in methanol).

Analysis for $C_{16}H_{21}O_3N_3$ (303.36): Calculated: C: 63.35; H: 6.98; N: 13.85. Found: C: 63.47; H: 7.16; N: 14.06.

(iv) N-Propionyl-L-alanyl-L-proline anilide 8.7 g (0.022 mol) of N-benzyloxycarbonyl-L-alanyl-L-proline anilide were dissolved in 40 ml of 4-N hydrogen bromide in acetic acid and the solution was stirred at room temperature for 1 hour. Upon addition of 300 ml of dry ether a white solid separated. It was allowed to settle. The solution was decanted off and the solid washed with two 150 ml portions of ether, dried on a rotary evaporator and dissolved in 120 ml of dry pyridine. 5.73 ml (0.044 mol) of propionic anhydride were added and the mixture was stirred at room temperature for 1 hour and then evaporated. The residue was dissolved in 250 ml of chloroform and the solution washed with 100 ml of 1-N hydrochloric acid, 100 ml of water and 100 ml of 5% sodium bicarbonate solution, dried over magnesium sulphate and evaporated to an oil. This oil crystallised from ethyl acetate/ether to yield 3.5 g of N-propionyl-L-alanyl-L-proline anilide. A second crop (1.5 g) was obtained from the mother liquor on allowing same to stand. The two crops were combined and chromatographed on 200 g of silica gel. 2% methanol/chloroform was used for the elution and 15 ml fractions were collected. Fractions 35–90 were combined and evaporated. The residue was recrystallised from ethyl acetate/petroleum ether to give 3.24 g (46%) of N-propionyl-L-alanyl-L-proline anilide of melting point 156°–157° C.; $[\alpha]_D^{20} = -188.7°$ (c = 1.034% in methanol).

Analysis for $C_{17}H_{23}O_3N_3$ (317.39): Calculated: C: 64.33; H: 7.30; N: 13.24. Found: C: 63.58; H: 7.50; N: 13.07; $H_2O$: 1.25. Water-free: C: 64.37; H: 7.45; N: 13.23.

(v) N-Benzoyl-L-alanyl-L-proline anilide 3 g (0.0076 mol) of N-benzyloxycarbonyl-L-alanyl-L-proline anilide were treated with 4-N hydrogen bromide in acetic acid in a manner analogous to that described in part (B)(ii) of this Example. The hydrobromide obtained was dissolved in 40 ml of dry pyridine and 1.75 ml (0.0052 mol) of benzoyl chloride were added. The solution was stirred at room temperature for 1 hour and then evaporated to an oil. This oil was dissolved in 120 ml of ethyl acetate and the solution was washed twice with two 80 ml portions of 5% citric acid solution, 80 ml of water, twice with two 80 ml portions of 5% sodium bicarbonate solution and twice with two 80 ml portions of water, dried over sodium sulphate and evaporated. The residue crystallised from ethyl acetate/petroleum ether and was further purified by chromatography on 100 g of silica gel using chloroform for the elution. Crystallisation from ethyl acetate/petroleum ether yielded 1.3 g (47%) of pure N-benzoyl-L-alanyl-L-proline anilide of melting point 98°-102° C.; $[\alpha]_D^{20} = -64.4°$ (c = 1.009% in methanol).

Analysis for $C_{21}H_{23}O_3N_3$ (365.44): Calculated: C: 69.03; H: 6.34; N: 11.50. Found: C: 68.83; H: 6.22; N: 11.46.

(vi) N-Pivaloyl-L-alanyl-L-proline anilide 1 g (0.00292 mol) of L-alanyl-L-proline anilide hydrobromide was dissolved in 20 ml of dry pyridine and 0.45 ml (0.00584 mol) of pivaloyl chloride was added. The mixture was stirred at room temperature for 1 hour and then evaporated. Final traces of pyridine were removed by addition of 10 ml of toluene and re-evaporation. The residue was dissolved in 80 ml of chloroform and the solution washed with 50 ml of saturated sodium chloride solution, dried over magnesium sulphate and evaporated to an oil. This oil crystallised from chloroform/petroleum ether to yield 0.8 g (80%) of N-pivaloyl-L-alaline-L-proline anilide of melting point 71°-74° C.; $[\alpha]_D^{20} = -134°$ (c = 1.062% in methanol).

Analysis for $C_{19}H_{27}O_3N_3$ (345.45): Calculated: C: 66.06; H: 7.88; N: 12.16. Found: C: 64.04; H: 7.95; N: 11.88; $H_2O$: 3.37. Water-free: C: 66.20; H: 7.84; N: 12.28.

(vii) N-Hexanoyl-L-alanyl-L-proline anilide 1 g (0.00292 mol) of L-alanyl-L-proline anilide hydrobromide was dissolved in 20 ml of dry pyridine and 1.39 ml (0.00584 mol) of hexanoic anhydride were added. The solution was stirred at room temperature for 1 hour and then evaporated. Final traces of pyridine were removed by addition of 10 ml of toluene and re-evaporation. The residue was dissolved in 80 ml of chloroform and the solution washed with 50 ml of saturated sodium chloride solution, dried over magnesium sulphate and evaporated to an oil. This oil crystallised from ethyl acetate/petroleum ether to give 0.9 g (86%) of N-hexanoyl-L-alanyl-L-proline anilide of melting point 113°-115° C.; $[\alpha]_D^{20} = -171.8°$ (c = 1.011% in methanol).

Analysis for $C_{20}H_{29}O_3N_3$ (359.47): Calculated: C: 66.83; H: 8.13; N: 11.69. Found: C: 66.71; H: 7.97; N: 11.88.

(viii) N-Trifluoroacetyl-L-alanyl-L-proline anilide 1.71 g (0.005 mol) of L-alanyl-L-proline anilide hydrobromide were dissolved in 20 ml of dry pyridine and 1.4 ml (0.01 mol) of trifluoroacetic anhydride were added. The mixture was stirred for 1.5 hours at room temperature and the pyridine was then removed by evaporation. The resulting oil was triturated with toluene, re-evaporated and the residue partitioned between 50 ml of dichloromethane and 50 ml of water. The aqueous layer was re-extracted with 40 ml of dichloromethane. The organic layers were combined, washed in sequence with 80 ml of 1-N hydrochloric acid, 80 ml of water and 80 ml of 5% sodium bicarbonate solution, dried over magnesium sulphate and evaporated to a solid. This solid was treated with petroleum ether, filtered off and dried to yield 1.58 g (89%) of N-trifluoroacetyl-L-alanyl-L-proline anilide of melting point 204°-207° C.; $[\alpha]_D^{20} = -134.4°$ (c = 0.98% in glacial acetic acid).

Analysis for $C_{16}H_{18}O_3N_3F_3$ (357.34): Calculated: C: 53.78; H: 5.08; N: 11.76; F: 15.95. Found: C: 53.51; H: 5.10; N: 11.58; F: 16.01.

(ix) N-Cyanoacetyl-L-alanyl-L-proline anilide 1.7 g (0.005 mol) of L-alanyl-L-proline anilide hydrobromide were dissolved in 50 ml of dichloromethane at 0° C. 0.42 g (0.005 mol) of cyanoacetic acid, 0.7 ml (0.005 mol) of triethylamine and 1.1 g of N,N-dicyclohexylcarbodiimide were added and the mixture was stirred at 0° C. overnight. The solvent was removed by evaporation, the residue suspended in 50 ml of ethyl acetate, the suspension filtered and the filtrate washed with 1-N hydrochloric acid, water, 5% sodium bicarbonate solution and water, dried over magnesium sulphate and evaporated to give a white solid. Recrystallisation of this solid from ethyl acetate yielded 0.6 g (37%) of N-cyanoacetyl-L-alanyl-L-proline anilide of melting point 183°-184° C.; $[\alpha]_D^{20} = -204.6°$ (c = 0.78% in methanol).

Analysis for $C_{17}H_{20}O_3N_4$ (328.38): Calculated: C: 62.18; H: 6.14; N: 17.06. Found: C: 61.99; H: 6.17; N: 17.24.

(x) N-(1-Adamantylcarbonyl)-L-alanyl-L-proline anilide 3.42 g (0.01 mol) of L-alanyl-L-proline anilide hydrobromide were suspended in 100 ml of dry tetrahydrofuran and the suspension was cooled to 0° C. There were then added 2.8 ml (0.02 mol) of triethylamine followed by 1.72 g (0.001 mol) of 1-adamantoyl chloride. The mixture was stirred at 0° C. for 0.5 hour and at room temperature for 2 hours and then evaporated. The residue was extracted twice with 40 ml of ethyl acetate each time. The combined ethyl acetate extracts were washed successively with two 20 ml portions of 1-N hydrochloric acid, 20 ml of water, two 20 ml portions of 5% sodium bicarbonate solution and two 20 ml portions of water, dried over magnesium sulphate and evaporated. The residue was crystallised from ether/petroleum ether and further purified by chromatography on 100 g of silica gel using chloroform for the elution. Evaporation of the chloroform eluate and crystallisation of the residue from ether/petroleum ether yielded 1.09 g (24%) of pure N-(1-adamantylcarbonyl-L-alanyl-L-proline anilide of melting point 119°-121° C.; $[\alpha]_D^{20} = -142.9°$ (c = 1% in methanol).

Analysis for $C_{25}H_{33}O_3N_3$ (423.56): Calculated: C: 70.89; H: 7.85; N: 9.92. Found: C: 70.86; H: 7.92; N: 9.84.

(xi) N-(1-Adamantylacetyl)-L-alanyl-L-proline anilide

In a manner analogous to that described in part (x) of this Example, from L-alanyl-L-proline anilide hydrobromide and 1-adamantylacetyl chloride there was obtained in 38% yield (recrystallised from ethyl acetate/petroleum ether) N-(1-adamantylacetyl)-L-alanyl-L-proline anilide of melting point 111°-113° C.; $[\alpha]_D^{20} = -136.7°$ (c = 0.98% in methanol).

Analysis for $C_{26}H_{35}O_3N_3$ (437.59): Calculated: C: 71.37; H: 8.06; N: 9.60. Found: C: 71.47; H: 8.05; N: 9.50.

(xii) N-(p-Toluenesulphonyl)-L-alanyl-L-proline anilide 1.71 g (0.005 mol) of L-alanyl-L-proline anilide hydrobromide were suspended in 20 ml of dichloromethane. To the suspension were added 22 ml of 0.5-N sodium hydroxide solution followed by 1.05 g (1.1 equivalents) of p-toluenesulphonyl chloride. The mixture was stirred vigorously for 90 minutes. 50 ml of dichloromethane were added, the organic layer was separated, washed with 50 ml of brine, dried over magnesium sulphate and evaporated to an oil which crystallised upon the addition of petroleum ether. The solid was filtered off, washed with petroleum ether and dried to yield 1.94 g (93%) of N-(p-toluenesulphonyl)-L-alanyl-L-proline anilide of melting point 145°–147° C.; $[\alpha]_D^{20} = -126.2°$ (c=1.00% in glacial acetic acid).

Analysis for $C_{21}H_{25}O_4N_3S$ (415.51): Calculated: C: 60.70; H: 6.06; N: 10.11; S: 7.72. Found: C: 59.83; H: 6.10; N: 9.88; S: 7.80; $H_2O$: 1.85. Water-free: C: 60.96; H: 6.00; N: 10.07; S: 7.95.

(xiii) N-Benzenesulphonyl-L-alanyl-L-proline anilide

In a manner analogous to that described in part (xii) of this Example, from L-alanyl-L-proline anilide hydrobromide and benzenesulphonyl chloride there was obtained in 60% yield (recrystallised from ethyl acetate/ether) N-benzenesulphonyl-L-alanyl-L-proline anilide of melting point 126°–127° C. $[\alpha]_D^{20} = -113.0°$ (c=0.96% in glacial acetic acid).

Analysis for $C_{20}H_{23}O_4N_3S$ (401.48): Calculated: C: 59.83; H: 5.78; N: 10.47. Found: C: 58.93; H: 5.87; N: 10.09; $H_2O$: 1.06. Water-free: C: 59.55; H: 5.81; N: 10.20.

(xiv) N-(4-Nitrobenzenesulphonyl)-L-alanyl-L-proline anilide

In a manner analogous to that described in part (xii) of this Example, from L-alanyl-L-proline anilide hydrobromide and 4-nitrobenzenesulphonyl chloride there was obtained in 83% yield (recrystallised from ethyl acetate/petroleum ether) N-(4-nitrobenzenesulphonyl)-L-alanyl-L-proline anilide of melting point 113°–115° C.; $[\alpha]_D^{20} = -60.6°$ (c=0.98% in dimethylformamide).

Analysis for $C_{20}H_{22}O_6N_4S$ (446.48): Calculated: C: 53.80; H: 4.97; N: 12.55. Found: C: 53.10; H: 5.05; N: 12.18; $H_2O$: 0.96. Water-free: C: 53.60; H: 4.99; N: 12.30.

(xv) N-(1-Naphthalenesulphonyl)-L-alanine-L-proline anilide

In a similar manner to that described in part (xii) of this Example, from L-alanyl-L-proline anilide hydrobromide and 1-naphthalenesulphonyl chloride there was obtained N-(1-naphthalenesulphonyl)-L-alanyl-L-proline anilide in a yield of 50% (recrystallised from ethyl acetate/ether); melting point 127°–130° C.

Analysis for $C_{24}H_{25}O_4N_3S$ (451.55): Calculated: C: 63.84; H: 5.58; N: 9.31. Found: C: 63.86; H: 5.56; N: 9.31.

(xvi) N-(1-Adamantylsulphinyl)-L-alanine-L-proline anilide

In a manner analogous to that described in part (xii) of this Example, from L-alanyl-L-proline anilide hydrobromide and 1-adamantanesulphinyl chloride [prepared as described by H. Stetter et al, Angew. Chem. Int. Ed. (England) 7(11), 894–5, 1968] there was obtained in 91% yield (crystallised from ether) N-(1-adamantylsulphinyl)-L-alanyl-L-proline anilide of melting point 157°–160° C.; $[\alpha]_D^{20} = -89.0°$ (c=1.02% in glacial acetic acid).

Analysis for $C_{24}H_{33}O_3N_3S$ (443.61): Calculated: C: 64.98; H: 7.50; N: 9.47. Found: C: 64.78; H: 7.31; N: 9.24.

(xvii) N-(1-Adamantylsulphonyl)-L-alanyl-L-proline anilide 8.88 g (0.02 ml) of N-(1-adamantylsulphinyl)-L-alanyl-L-proline anilide, prepared as described in part (xvi) of this Example, were dissolved in 40 ml of glacial acetic acid and 10 ml of 30% hydrogen peroxide were added. The solution was heated to 65° C. for 2 hours, then cooled and evaporated to half of the original volume. 200 ml of water were added, whereby an oil precipitated. This oil was extracted into two 150 ml portions of ethyl acetate. The ethyl acetate extracts were combined and washed with two 150 ml portions of 5% sodium bicarbonate solution and 150 ml of water, dried over sodium sulphate and evaporated. The residue crystallized slowly from ether to yield 6.58 g of impure product which was further purified by column chromatography on 250 g of silica gel using chloroform for the elution. After evaporation of the chloroform eluate, there were obtained 3.2 g (35%) of N-(1-adamantylsulphonyl)-L-alanyl-L-proline anilide of melting point 138°–141° C.; $[\alpha]_D^{20} = -102.3°$ (c=1.03% in glacial acetic acid).

Analysis for $C_{24}H_{33}O_4N_3S$ (459.61): Calculated: C: 62.72; H: 7.24; N: 9.14. Found: C: 62.70; H: 7.38; N: 8.97.

(xviii) N-(D-10-Camphorsulphonyl)-L-alanyl-L-proline anilide

In a manner analogous to that described in part (xii) of this Example, from L-alanyl-L-proline anilide hydrobromide and D-10-camphorsulphonyl chloride there was obtained in 43% yield (recrystallised from ether) N-(D-10-camphorsulphonyl)-L-alanyl-L-proline anilide of melting point 180°–182° C.; $[\alpha]_D^{20} = -100.3°$ (c=0.97% in methanol).

Analysis for $C_{24}H_{33}O_5N_3S$ (475.61): Calculated: C: 60.61; H: 6.99; N: 8.84. Found: C: 60.51; H: 7.02; N: 8.85.

(xix) N-(4-Acetylaminobenzenesulphonyl)-L-alanyl-L-proline anilide

In a manner analogous to that described in part (xii) of this Example, from L-alanyl-L-proline anilide hydrobromide and p-acetylaminobenzenesulphonyl chloride there was obtained in 37% yield (recrystallised from ethyl acetate/petroleum ether) N-(4-acetylaminobenzenesulphonyl)-L-alanyl-L-proline anilide of melting point 140°–142° C.; $[\alpha]_D^{20} = -145.3°$ (c=0.99% in methanol).

Analysis for $C_{22}H_{26}O_5N_4S$ (458.54): Calculated: C: 57.63; H: 5.72; N: 12.22. Found: C: 56.70; H: 5.69; N: 11.86; $H_2O$: 1.94. Water-free: C: 57.81; H: 5.80; N: 12.09.

(xx) N-(4-Methoxybenezenesulphonyl)-L-alanyl-L-proline anilide

In a manner analogous to that described in part (xii) of this Example, from L-alanyl-L-proline anilide hydrobromide and 4-methoxybenzenesulphonyl chloride there was obtained in 76% yield (recrystallised from ethyl acetate/ether) N-(4-methoxybenzenesulphonyl)-L-alanyl-L-proline anilide of melting point 153°–154° C.; $[\alpha]_D^{20} = -131.3°$ (c=1.00% in glacial acetic acid).

Analysis for $C_{21}H_{25}O_5N_3S$ (431.51): Calculated: C: 58.45; H: 5.84; N: 9.74. Found: C: 58.28; H: 5.77; N: 9.86.

(xxi) N-(Mesitylenesulphonyl)-L-alanyl-L-proline anilide

In a manner analogous to that described in part (xii) of this Example, from L-alanyl-L-proline anilide hydrobromide and mesitylenesulphonyl chloride there was obtained in 53% yield (recrystallised from ethyl acetate/ether) N-(mesitylenesulphonyl)-L-alanyl-L-proline anilide of melting point 162°–163.5° C.; $[\alpha]_D^{20} = -130.7°$ (c=0.98% in glacial acetic acid).

Analysis for $C_{23}H_{29}O_4N_3S$ (443.56): Calculated: C: 62.28; H: 6.59; N: 9.47. Found: C: 62.12; H: 6.55; N: 9.45.

EXAMPLE 5

(A) The preparation of the starting material:
N-Benzyloxycarbonyl-L-alanyl-L-proline This compound was prepared as described in Example 3(A).

(B) The process:

(i) N-Benzyloxycarbonyl-L-alanyl-L-proline 4-nitroanilide 3.2 g (0.01 mole) of N-benzyloxycarbonyl-L-alanyl-L-proline were dissolved in 50 ml of dry tetrahydrofuran and the solution was cooled to −10° C. 1.27 ml (0.01 mol) of N-ethylmorpholine were added followed by 1.31 ml (0.1 mol) of isobutyl chloroformate and the mixture was stirred at −10° C. for 20 minutes. 1.38 g (0.01 mol) of 4-nitroaniline were then added, the mixture was stirred at 0° C. for 1 hour and then left to stand at room temperature for 72 hours. The mixture was then evaporated and the residue dissolved in 100 ml of ethyl acetate. The solution was washed with 80 ml of 1-N hydrochloric acid, 80 ml of water and 80 ml of 5% sodium bicarbonate solution, dried over magnesium sulphate and evaporated. The resulting oil was chromatographed on 100 g of silica gel using chloroform for the elution. The residue obtained after evaporating the chloroform eluate was taken up in ether and left to stand for 16 hours, the pure crystalline N-benzyloxycarbonyl-L-alanyl-L-proline 4-nitroanilide separating out. The yield was 1.5 g (34%) and the melting point 160°–163° C.; $[\alpha]_D^{20} = -178.1°$ (c=0.975% in methanol).

Analysis for $C_{22}H_{24}O_6N_4$ (440.46): Calculated: C: 59.99; H: 5.49; N: 12.72. Found: C: 59.74; H: 5.67; N: 12.51.

(ii) N-Propionyl-L-alanyl-L-proline 4-nitroanilide 1.1 g (0.0025 mol) of N-benzyloxycarbonyl-L-alanyl-L-proline 4-nitroanilide were dissolved in 10 ml of 4-N hydrogen bromide in acetic acid and the mixture was stirred at room temperature for 1 hour. 80 ml of dry ether was added. An oil precipitated and was allowed to settle out. The solution was decanted off and the oil was washed with two 80 ml portions of ether and then dissolved in 20 ml of dry pyridine. 0.64 ml (0.005 mol) of propionic anhydride was added and the solution stirred at room temperature for 1 hour. The solution was then evaporated. Final traces of pyridine were removed by addition of 50 ml of toluene and re-evaporation. The residue was dissolved in 100 ml of chloroform and the solution was washed twice with 80 ml of water each time, dried over magnesium sulphate and evaporated to give an oil. The desired N-propionyl-L-alanyl-L-proline 4-nitroanilide crystallised from ethyl acetate/petroleum ether in a yield of 0.62 g (68%) and with a melting point of 183°–186° C.; $[\alpha]_D^{20} = -211.6°$ (c=1.014% in methanol).

Analysis for $C_{17}H_{22}O_5N_4$ (362.39): Calculated: C: 56.35; H: 6.12; N: 15.46. Found: C: 56.33; H: 6.21; N: 15.46.

EXAMPLE 6

(A) The preparation of the starting marterial:
N-Benzyloxycarbonyl-L-alanyl-L-proline This compound was prepared as described in Example 3(A).
(B) The process:
 (i) N-Benzyloxycarbonyl-L-alanyl-L-proline 4-methoxyanilide In a manner analogous to that described in Example 3(B)(i) from N-benzyloxycarbonyl-L-alanyl-L-proline and 4-methoxyaniline there was obtained N-benzyloxycarbonyl-L-alanyl-L-proline 4-methoxyanilide in a yield of 69% (recrystallised from ethyl acetate/ether); melting point 163°–164° C.; $[\alpha]_D^{20} = -150.9°$ (c=1% in methanol).

Analysis for $C_{23}H_{27}O_5N_3$ (425.49): Calculated: C: 64.93; H: 6.40; N: 9.87. Found: C: 64.79; H: 6.57; N: 9.76.

(ii) N-Propionyl-L-alanyl-L-proline 4-methoxyanilide

In a manner analogous to that described in Example 3(B)(ii), from N-benzyloxycarbonyl-L-alanyl-L-proline 4-methoxyanilide there was obtained N-propionyl-L-alanyl-L-proline 4-methoxyanilide in a yield of 52% (recrystallised from ethyl acetate); melting point 169°–171° C.; $[\alpha]_D^{20} = -191.6°$ (c=1.02% in methanol).

Analysis for $C_{18}H_{25}O_4N_3$ (347.42): Calculated: C: 62.63; H: 7.25; N: 12.09. Found: C: 62.16; H: 7.16; N: 11.99.

EXAMPLE 7

(A) The preparation of the starting material:
N-Benzyloxycarbonyl-L-alanyl-L-proline This compound was prepared as described in Example 3(A)
(B) The process:
 (i) N-Benzyloxycarbonyl-L-alanyl-L-proline cyclopentylamide 6.4 g (0.02 mol) of N-benzyloxycarbonyl-L-alanyl-L-proline were dissolved in 100 ml of dry tetrahydrofuran and the solution was cooled to −10° C. 2.54 ml of N-ethylmorpholine and 2.62 ml of isobutyl chloroformate were added and the mixture was stirred at −10° C. for 20 minutes. 1.98 ml of cyclopentylamine were then added and the mixture was stirred at 0° C. for 1 hour and then at room temperature overnight. The mixture was then evaporated and the product which crystallised on the addition of water was extracted into ethyl acetate. The organic layer was washed neutral, dried over sodium sulphate and evaporated, the product crystallising on the addition of ether. There were obtained 4.8 g (71%) of N-benzyloxycarbonyl-L-alanyl-L-proline cyclopentylamide of melting point 118°–119° C.; $[\alpha]_D^{20} = -93.5°$ (c=1.0228% in methanol).

Analysis for $C_{21}H_{29}O_4N_3$ (387.48): Calculated: C: 65.10; H: 7.54; N: 10.84. Found: C: 65.05; H: 7.47; N: 10.79.

(ii) L-Alanyl-L-proline cyclopentylamide hydrobromide 3.9 g of N-benzyloxycarbonyl-L-alanyl-L-proline cyclopentylamide were treated with 4-N hydrogen bromide in acetic acid in a manner analogous to that described in Example 8(B)(ii) hereinafter. There were thus obtained 3.3 g (99%) of L-alanyl-L-proline cyclopentylamide hydrobromide of melting point 209°–212° C.

(iii) N-Propionyl-L-alanyl-L-proline cyclopentylamide

The L-alanyl-L-proline cyclopentylamide hydrobromide obtained according to part (B)(ii) of this Example was dissolved in 40 ml of pyridine and the solution was treated with 2.6 ml of propionic anhydride. The mixture was stirred at room temperature for 2 hours. The mixture was then evaporated, final traces of pyridine being removed by addition of toluene and re-evaporation. The residue was recrystallised from ethyl acetate to give 2.1 g of N-propionyl-L-alanyl-L-proline cyclopentylamide of melting point 172°–173° C.; $[\alpha]_D^{20} = -122.8°$ (c=1.0314% in methanol).

Analysis for $C_{16}H_{27}O_3N_3$ (309.41): Calculated: C: 62.11; H: 8.80; N: 13.58. Found: C: 62.27; H: 8.85; N: 13.59.

EXAMPLE 8

(A) The preparation of the starting material:
N-Benzyloxycarbonyl-L-alanyl-L-proline This compound was prepared as described in Example 3(A).

(B) The process:

(i) N-Benzyloxycarbonyl-L-alanyl-L-proline cyclohexylamide 3.2 g (0.01 mol) of N-benzyloxycarbonyl-L-alanyl-L-proline were dissolved in 50 ml of dry tetrahydrofuran and the solution was cooled to −10° C. 1.27 ml (0.01 mol) of N-ethylmorpholine were added followed by 1.31 ml (0.01 mol) of isobutyl chloroformate and the solution was stirred at −10° C. for 20 minutes. 1.21 ml (0.01 mol) of cyclohexylamine were then added and the mixture was stirred at 0° C. for 1 hour and then left to stand at room temperature for 16 hours. The mixture was evaporated and the residue was treated with 100 ml of ethyl acetate, washed with 80 ml of 1-N hydrochloric acid, 80 ml of water and 80 ml of 5% sodium bicarbonate solution, dried over sodium sulphate and evaporated to an oil. The product crystallised from ethyl acetate/ethyl to yield 2.36 g of N-benzyloxycarbonyl-L-alanyl-L-proline cyclohexylamide of melting point 130.5°–131.5° C. A second crop (0.95 g; melting point 130.5°–131.5° C.) was obtained on leaving the mother liquor to stand overnight. The total yield was 83%, $[\alpha]_D^{20} = -96.3°$ (c = 1.175% in methanol).

Analysis for $C_{22}H_{31}O_4N_3$ (401.51): Calculated: C: 65.81; H: 7.78; N: 10.47. Found: C: 65.71; H: 7.66; N: 10.54.

(ii) L-Alanyl-L-proline cyclohexylamide hydrobromide 2 g (0.005 mol) of N-benzyloxycarbonyl-L-alanyl-L-proline cyclohexylamide were dissolved in 10 ml of 4-N hydrogen bromide in acetic acid and the mixture was stirred at room temperature for 1 hour. 100 ml of dry ether were then added. An oil precipitated and was allowed to settle. The solution was decanted off, the oil washed with 100 ml of ether, dissolved in the minimum volume of methanol and an excess of ethyl acetate added. Crystallisation soon took place and there were obtained 1.75 g (100%) of L-alanyl-L-proline cyclohexylamide hydrobromide of melting point 233°–236° C.

(iii) N-Propionyl-L-alanyl-L-proline cyclohexylamide 1.75 g (0.00502 mol) of L-alanyl-L-proline cyclohexylamide hydrobromide were dissolved in 30 ml of dry pyridine and 1.3 ml (0.01 mol) of propionic anhydride were added. The solution was stirred at room temperature for 2 hours and then evaporated. Final traces of pyridine were removed by addition of 15 ml of toluene and re-evaporation. The residue was dissolved in 80 ml of chloroform and the solution washed with two 50 ml portions of water, dried over magnesium sulphate and evaporated to a white solid which was recrystallised from ethyl acetate to give 1.05 g (65%) of N-propionyl-L-alanyl-L-proline cyclohexylamide of melting point 172°–174° C.; $[\alpha]_D^{20} = -125.1°$ (c = 0.991% in methanol).

Analysis for $C_{17}H_{29}O_3N_3$ (323.44): Calculated: C: 63.13; H: 9.04; N: 12.99. Found: C: 63.10; H: 8.75; N: 12.78.

(iv) N-(p-Toluenesulphonyl)-L-alanyl-L-proline cyclohexylamide hemihydrate

In a manner analogous to that described in Example 4(B)(xii), from L-alanyl-L-proline cyclohexylamide hydrobromide and p-toluenesulphonyl chloride there was obtained in 79% yield (crystallised from ethyl acetate after 7 days at 4° C.) N-(p-toluenesulphonyl)-L-alanyl-L-proline cyclohexylamide of melting point 85°–88° C.; $[\alpha]_D^{20} = -83.2°$ (c = 1.02% in glacial acetic acid).

Analysis for $C_{21}H_{31}O_4N_3S.0.5H_2O$ (430.56): Calculated: C: 58.58; H: 7.49; N: 9.68. Found: C: 58.29; H: 7.30; N: 9.76.

EXAMPLE 9

(A) The preparation of the starting material: N-Benzyloxycarbonyl-L-alanyl-L-proline This compound was prepared as described in Example 3(A).

(B) The process:

(i) N-Benzyloxycarbonyl-L-alanyl-L-proline cycloheptylamide 6.4 g (0.02 mol) of N-benzyloxycarbonyl-L-alanyl-L-proline were dissolved in 75 ml of dry tetrahydrofuran and the solution was cooled to −10° C. 2.54 ml (0.02 mol) of N-ethylmorpholine and 2.62 ml (0.02 mol) of isobutyl chloroformate were added and the solution was stirred at −10° C. for 20 minutes. A solution of 2.25 g (0.02 mol) of cycloheptylamine in 25 ml of dry tetrahydrofuran was then added. The mixture was stirred at 0° C. for 1 hour and then left to stand at room temperature for 16 hours. The mixture was then evaporated and the residue extracted twice with 50 ml of ethyl acetate each time. The combined ethyl acetate extracts were washed successively with 1-N hydrochloric acid, water, 5% sodium bicarbonate solution and water and then dried over magnesium sulphate. Evaporation yielded an oil which solidified upon trituration with petroleum ether. The solid was recrystallised from ethyl acetate/petroleum ether to yield 5.6 g (67.5%) of N-benzyloxycarbonyl-L-alanyl-L-proline cycloheptylamide of melting point 110°–113° C.; $[\alpha]_D^{20} = -92.4°$ (c = 1.05% in methanol).

Analysis for $C_{23}H_{33}O_4N_3$ (415.54): Calculated: C: 66.48; H: 8.00; N: 10.11. Found: C: 66.32; H: 7.98; N: 10.22.

(ii) N-Propionyl-L-alanyl-L-proline cycloheptylamide 2.6 g (0.0063 mol) of N-benzyloxycarbonyl-L-alanyl-L-proline cycloheptylamide were dissolved in 15 ml of 4-N hydrogen bromide in acetic acid and the mixture was stirred at room temperature for 1 hour. 100 ml of anhydrous ether were added and an oil precipitated from the solution. The ether phase was decanted off and the oil washed with 100 ml of anhydrous ether. The ether layer was again decanted off and the oil dissolved in 30 ml of dry pyridine. 1.6 g (0.0126 mol) of propionic anhydride were added and the solution was stirred at room temperature for 2 hours. The pyridine was removed by evaporation, 50 ml of toluene were added to the residue and the mixture was again evaporated. The solid residue was taken up in 100 ml of chloroform and the solution was washed with sodium chloride solution and dried over magnesium sulphate. The chloroform was removed by evaporation to yield an oil. This oil was dissolved in the minimum volume of ether and petroleum ether was added, whereby a white solid crystallised out of the solution. There was obtained 1.85 g (88.1%) of N-propionyl-L-alanyl-L-proline cycloheptylamide of melting point 155°–156° C. $[\alpha]_D^{20} = -119.4°$ (c = 0.91% in methanol).

Analysis for $C_{18}H_{31}O_3N_3$ (337.47): Calculated: C: 64.07; H: 9.26; N: 12.45. Found: C: 63.91; H: 9.14; N: 12.50.

EXAMPLE 10

(A) The preparation of the starting material:
N-Benzyloxycarbonyl-L-alanyl-L-proline This compound was prepared as described in Example 3(A).

(B) The process:

(i) N-Benzyloxycarbonyl-L-alanyl-L-proline cyclooctylamide 6.4 g (0.02 mol) of N-benzyloxycarbonyl-L-alanyl-L-proline were dissolved in 75 ml of dry tetrahydrofuran and the solution was cooled to −10° C. 2.54 ml (0.02 mol) of N-ethylmorpholine and 2.62 ml (0.02 mol) of isobutyl chloroformate were added and the resulting solution was stirred at −10° C. for 20 minutes. A solution of 2.5 g (0.02 mol) of cyclooctylamine in 25 ml of dry tetrahydrofuran was then added. The resulting mixture was stirred at 0° C. for 1 hour and then left to stand at room temperature for 16 hours. The tetrahydrofuran was removed by evaporation and the residue extracted with two 50 ml portions of ethyl acetate. The combined ethyl acetate extracts were washed successively with 1-N hydrochloric acid, water, 5% sodium bicarbonate solution and water and then dried over magnesium sulphate. Evaporation yielded an oil which solidified upon trituration with ether/petroleum ether. After recrystallisation from ethyl acetate/petroleum ether, there were obtained 5.1 g (59.3%) of N-benzyloxycarbonyl-L-alanyl-L-proline cyclooctylamide of melting point 94°–96° C.; $[\alpha]_D^{20} = -95.0°$ (c = 1.02% in methanol).

Analysis for $C_{24}H_{35}O_4N_3$ (429.56): Calculated: C: 67.11; H: 8.21; N: 9.78. Found: C: 67.11; H: 8.07; N: 9.72.

(ii) N-Propionyl-L-alanyl-L-proline cyclooctylamide 2 g (0.0047 mol) of N-benzyloxycarbonyl-L-alanyl-L-proline cyclooctylamide were dissolved in 10 ml of 4-N hydrogen bromide in acetic acid and the solution was stirred at room temperature for 1 hour. 100 ml of anhydrous ether were added and an oil precipitated out of the solution. The ether layer was decanted off and the oil washed with 100 ml of anhydrous ether. The ether layer was again decanted off and the oil dissolved in 30 ml of dry pyridine. 1.2 g (0.0094 mol) of propionic anhydride were added and the solution was stirred at room temperature for 2 hours. The pyridine was removed by evaporation, 50 ml of toluene were added to the residue and the mixture was again evaporated in order to azeotropically remove any residual pyridine. The solid obtained was taken up in 100 ml of chloroform, the solution was washed with sodium chloride solution and dried over magnesium sulphate. The solution was then evaporated to yield an oil. This oil was dissolved in the minimum volume of ether and petroleum ether was added, whereby a white solid crystallised out of the solution. There was obtained 0.900 g (56.3%) of N-propionyl-L-alanyl-L-proline cyclooctylamide of melting point 142°–143° C.; $[\alpha]_D^{20} = -120.3°$ (c = 0.82% in methanol).

Analysis for $C_{19}H_{33}N_3O_3$ (351.49): Calculated: C: 64.93; H: 9.46; N: 11.95. Found: C: 64.76; H: 9.39; N: 11.84.

EXAMPLE 11

(A) The preparation of the starting material:
N-Benzyloxycarbonyl-L-alanyl-L-proline This compound was prepared as described in Example 3(A).

(B) The process:

N-Benzyloxycarbonyl-L-alanyl-L-proline n-pentylamide 2 g (0.06 mol) of N-benzyloxycarbonyl-L-alanyl-L-proline were dissolved in 20 ml of dry tetrahydrofuran and the solution was cooled to −10° C. 0.76 ml (0.06 mol) of N-ethylmorpholine and 0.79 ml (0.006 mol) of isobutyl chloroformate were added and the resulting mixture was stirred at −10° C. for 20 minutes. 0.69 ml (0.006 mol) of n-pentylamine was then added and the resulting solution was stirred at −20° C. for 1 hour and then left to stand at room temperature overnight. The solution was then evaporated to an oil which was dissolved in ethyl acetate. The ethyl acetate solution was washed twice with water, twice with 5% citric acid solution, once with water, twice with 5% sodium bicarbonate solution and twice with water, dried and evaporated to an oil. The desired N-benzyloxycarbonyl-L-alanyl-L-proline n-pentylamide was crystallised from ethyl acetate/petroleum ether in a yield of 1 g (42.8%) and with a melting point of 102°–104° C.

EXAMPLE 12

(A) The preparation of the starting material:

(i) N-Benzyloxycarbonyl-L-proline n-pentylamide 12.46 g (0.05 mol) of N-benzyloxycarbonyl-L-proline were dissolved in 100 ml of dry tetrahydrofuran and the solution was cooled to −10° C. The solution was stirred and there were added thereto 6.56 ml (0.05 mol) of isobutyl chloroformate and 6.35 ml (0.05 mol) of N-ethylmorpholine. The mixture was then stirred at −10° C. for 15 minutes. 5.76 ml (0.05 mol) of n-pentylamine were then added and the resulting mixture was stirred at 0° C. for 1 hour and then at room temperature for 16 hours. The mixture was evaporated to an oil and 400 ml of water were added. The resulting mixture was extracted with two 150 ml portions of ethyl acetate, the organic layers were combined and washed successively with two 100 ml portions of 5% citric acid solution, once with 100 ml of water, twice with 100 ml portions of 5% sodium bicarbonate solution and once with 100 ml of water. The organic layer was dried over sodium sulphate, evaporated to an oil and triturated with 350 ml of petroleum ether. On scratching, the product crystallized out, was filtered off and washed with 100 ml of petroleum ether. There were thus obtained 10.16 g (64%) of N-benzyloxycarbonyl-L-proline n-pentylamide of melting point 74°–76° C. A second crop (0.800 g) of melting point 76°–79° C. was obtained from the mother liquor.

(ii) L-Proline n-pentylamide hydrobromide 5 g of N-benzyloxycarbonyl-L-proline n-pentylamide were dissolved in 20 ml of 4-N hydrogen bromide in acetic acid and the mixture was stirred for 1 hour. 150 ml of dry ether were then added. A clear oil precipitated out and was allowed to settle. The ether was decanted off and the oil washed with a further 100 ml of dry ether. Evaporation yielded 3.4 g (82%) of L-proline n-pentylamide in the form of an oil.

(B) The process:

(i) N-Benzyloxycarbonyl-L-alanyl-L-proline n-pentylamide 2.86 g (0.0128 mol) of N-benzyloxycarbonyl-L-alanine were dissolved in 20 ml of dry tetrahydrofuran and the mixture was cooled to −10° C. 1.63 ml (0.0128 mol) of N-ethylmorpholine and 1.68 ml (0.0128 mol) of isobutyl chloroformate were added and the mixture was stirred at −10° C. for 15–20 minutes.

3.4 g (0.0128 mol) of L-proline n-pentylamide hydrobromide were dissolved in 20 ml of dry dimethylformamide and the solution was cooled to 0° C. 2 ml of N-ethylmorpholine were then added to this solution. The resulting mixture was combined with the mixed anhydride solution prepared as described in the preceding paragraph, stirred at 0° C. for 1 hour and then at room temperature overnight. Evaporation of the solvents yielded an oil which was dissolved in 150 ml of ethyl acetate and washed successively with two 60 ml portions of 5% citric acid solution, 60 ml of water, two 60 ml portions of 5% sodium bicarbonate solution and 60 ml of water. The organic phase was dried over magnesium sulphate and evaporated to give an oil which soon crystallised. Recrystallisation from ethyl acetate/petroleum ether yielded 2.7 g (54%) of N-benzyloxycarbonyl-L-alanyl-L-proline n-pentylamide of melting point 103°–105° C.; $[\alpha]_D^{20} = -94.6°$ (c=1.114% in methanol).

Analysis for $C_{21}H_{31}O_4N_3$ (389.50): Calculated: C: 64.76; H: 8.02; N: 10.79. Found: C: 64.79; H: 8.14; N: 10.87.

(ii) L-Alanyl-L-proline n-pentylamide 2.5 g of N-benzyloxycarbonyl-L-alanyl-L-proline n-pentylamide were dissolved in 15 ml of 4-N hydrogen bromide in acetic acid and the solution was stirred for 1 hour at room temperature. 150 ml of dry ether were added. An oil precipitated out and was allowed to settle. The ether was decanted off and the procedure repeated using 150 ml of fresh ether. On evaporation there were obtained 2.5 g of L-alanyl-L-proline n-pentylamide in the form of a white solid.

(iii) N-Propionyl-L-alanyl-L-proline n-pentylamide 2.15 g (0.0064 mol) of L-alanyl-L-proline n-pentylamide was dissolved in 40 ml of dry pyridine and 3.6 ml of propionic anhydride were added to the solution. The mixture was stirred at room temperature for 1.5 hours. The solution was then evaporated to an oil which was dissolved in 150 ml of chloroform and washed with 50 ml of 5% citric acid solution, 50 ml of water and 50 ml of 5% sodium bicarbonate solution. The organic phase was dried over magnesium sulphate and evaporated to an oil. This oil was crystallised from ethyl acetate/petroleum ether to give 1.16 g of N-propionyl-L-alanyl-L-proline n-pentylamide of melting point 105°–108° C.; $[\alpha]_D^{20} = -151.7°$ (c=1.114% in water).

Analysis for $C_{16}H_{29}O_3N_3$ (311.43): Calculated: C: 61.71; H: 9.39; N: 13.49. Found: C: 61.49; H: 9.45; N: 13.60.

The following Example illustrates pharmaceutical preparations containing the dipeptide derivatives provided by the present invention:

EXAMPLE A

An aerosol composition can contain the following ingredients:

| Ingredient | Percent by weight |
|---|---|
| Dipeptide derivative | 1–5 |
| Ethanol | 15–35 |
| Propellant* | ad 100 |

*The propellant can be dichlorodifluoromethane or 5:1 mixture of dichlorotetrafluoroethane and dichlorotetrafluoromethane.

We claim:
1. Dipeptide derivatives of the formula

$$R^3-NH-\underset{(L)}{CH}(CH_3)-CO-N(R^2)-\underset{*}{CH}(R^1)-CO-NH-R \quad (I)$$

wherein R is phenyl, substituted phenyl, lower cycloalkyl or n-($C_4$-$C_6$)-alkyl; $R^1$ and $R^2$ each is hydrogen or methyl, with the proviso that $R^1$ and $R^2$ are not simultaneously hydrogen, or $R^1$ and $R^2$ together are trimethylene; $R^3$ is alkanoyl, halo-alkanoyl, nitro-alkanoyl, cyano-alkanoyl, cycloalkylcarbonyl, cycloalkyl-alkanoyl, aroyl, aryl-alkanoyl, alkoxycarbonyl, aryloxycarbonyl, arylsulfonyl, alkylsulfonyl, cyclo-alkylsulfonyl, cycloalkylsulfinyl, cycloalkyl-alkylsulfonyl or cycloalkyl-alkylsulfinyl and the asterisk denotes that the configuration at the carbon atom so-marked is L when $R^1$ is other than hydrogen.

2. Dipeptide derivatives of claim 1 wherein $R^1$ is hydrogen and $R^2$ is methyl or $R^1$ and $R^2$ together are trimethylene.

3. Dipeptide derivatives of claim 1 wherein R is phenyl.

4. The compound of claim 1 which is N-acetyl-L-alanyl-L-proline anilide.

5. The compound of claim 1 which is N-propionyl-L-alanyl-L-proline anilide.

6. The compound of claim 1 which is N-benzoyl-L-alanyl-L-proline anilide.

7. The compound of claim 1 which is N-pivaloyl-L-alanyl-L-proline anilide.

8. The compound of claim 1 which is N-hexanoyl-L-alanyl-L-proline anilide.

9. The compound of claim 1 which is N-trifluoroacetyl-L-alanyl-L-proline anilide.

10. The compound of claim 1 which is N-cyanoacetyl-L-alanyl-L-proline anilide.

11. The compound of claim 1 which is N-(1-adamantylcarbonyl)-L-alanyl-L-proline anilide.

12. The compound of claim 1 which is N-(1-adamantylacetyl)-L-alanyl-L-proline anilide.

13. The compound of claim 1 which is N-(p-toluenesulfonyl)-L-alanyl-L-proline anilide.

14. The compound of claim 1 which is N-benzenesulfonyl-L-alanyl-L-proline anilide.

15. The compound of claim 1 which is N-(4-nitrobenzenesulfonyl)-L-alanyl-L-proline anilide.

16. The compound of claim 1 which is N-(1-naphthalenesulfonyl)-L-alanyl-L-proline anilide.

17. The compound of claim 1 which is N-(1-adamantylsulfinyl)-L-alanyl-L-proline anilide.

18. The compound of claim 1 which is N-(1-adamantylsulfonyl)-L-alanyl-L-proline anilide.

19. The compound of claim 1 which is N-(D-10-camphorsulfonyl)-L-alanyl-L-proline anilide.

20. The compound of claim 1 which is N-(4-acetylaminobenzenesulfonyl)-L-alanyl-L-proline anilide.

21. The compound of claim 1 which is N-(4-methoxybenzenesulfonyl)-L-alanyl-L-proline anilide.

22. The compound of claim 1 which is N-mesitylenesulfonyl-L-alanyl-L-proline anilide.

23. The compound of claim 1 which is N-propionyl-L-alanyl-L-proline 2,4-dichloroanilide.

24. The compound of claim 1 which is N-propionyl-L-alanyl-L-proline 4-nitroanilide.

25. The compound of claim 1 which is N-propionyl-L-alanyl-L-proline 4-methoxyanilide.

26. The compound of claim 1 which is N-propionyl-L-alanyl-L-proline cyclopentylamide.

27. The compound of claim 1 which is N-propionyl-L-alanyl-L-proline cyclohexylamide.

28. The compound of claim 1 which is N-(p-toluenesulfonyl)-L-alanyl-L-proline cyclohexylamide.

29. The compound of claim 1 which is N-propionyl-L-alanyl-L-proline cycloheptylamide.

30. The compound of claim 1 which is N-propionyl-L-alanyl-L-proline cyclooctylamide.

31. The compound of claim 1 which is N-propionyl-L-alanyl-L-alanine anilide.

32. The compound of claim 1 which is N-benzoyl-L-alanyl-L-alanine anilide.

33. The compound of claim 1 which is N-propionyl-L-alanyl-L-alanine cyclohexylamide.

34. The compound of claim 1 which is N-propionyl-L-alanyl-L-proline n-pentylamide.

* * * * *